United States Patent
Hallberg

(10) Patent No.: US 9,883,820 B2
(45) Date of Patent: Feb. 6, 2018

(54) METHOD AND ENGINE FOR DEFINING RESPIRATION EVENTS IN BODY SENSOR SIGNALS

(71) Applicant: Sharp Laboratories of America, Inc., Camas, WA (US)

(72) Inventor: Bryan Severt Hallberg, Vancouver, WA (US)

(73) Assignee: Sharp Laboratories of America, Inc., Camas, WA (US)

( * ) Notice: Subject to any disclaimer, the term of this patent is extended or adjusted under 35 U.S.C. 154(b) by 231 days.

(21) Appl. No.: 14/231,275

(22) Filed: Mar. 31, 2014

(65) Prior Publication Data

US 2015/0272476 A1 Oct. 1, 2015

(51) Int. Cl.
| | | |
|---|---|---|
| *G01N 33/48* | (2006.01) | |
| *A61B 5/08* | (2006.01) | |
| *G06F 19/00* | (2011.01) | |
| *G06G 7/58* | (2006.01) | |
| *A61B 5/00* | (2006.01) | |

(52) U.S. Cl.
CPC ............ *A61B 5/0816* (2013.01); *G06F 19/32* (2013.01); *A61B 5/082* (2013.01); *A61B 5/7264* (2013.01); *A61B 5/7275* (2013.01)

(58) Field of Classification Search
None
See application file for complete search history.

(56) References Cited

U.S. PATENT DOCUMENTS

| | | |
|---|---|---|
| 6,771,804 B1 | 8/2004 | Maetschke |
| 8,485,982 B2 | 7/2013 | Gavish et al. |
| 2007/0282212 A1 | 12/2007 | Sierra et al. |
| 2010/0262031 A1 | 10/2010 | Fu et al. |
| 2012/0253215 A1 | 10/2012 | Fu et al. |
| 2013/0090567 A1 | 4/2013 | Lee et al. |

FOREIGN PATENT DOCUMENTS

| | | |
|---|---|---|
| JP | 2012-157558 | 8/2012 |
| JP | 2013-123494 | 6/2013 |

*Primary Examiner* — Eric S Dejong
(74) *Attorney, Agent, or Firm* — Steven M. Reiss; ScienBizIP, P.C.

(57) ABSTRACT

The present invention provides a method and engine for defining respiration events in body sensor signals that are highly accurate and compatible with many different classes of respiration monitoring devices. The present method and engine provide improved respiration event definition through the expedients of dynamic thresholding, segment merging and tail identification.

4 Claims, 9 Drawing Sheets

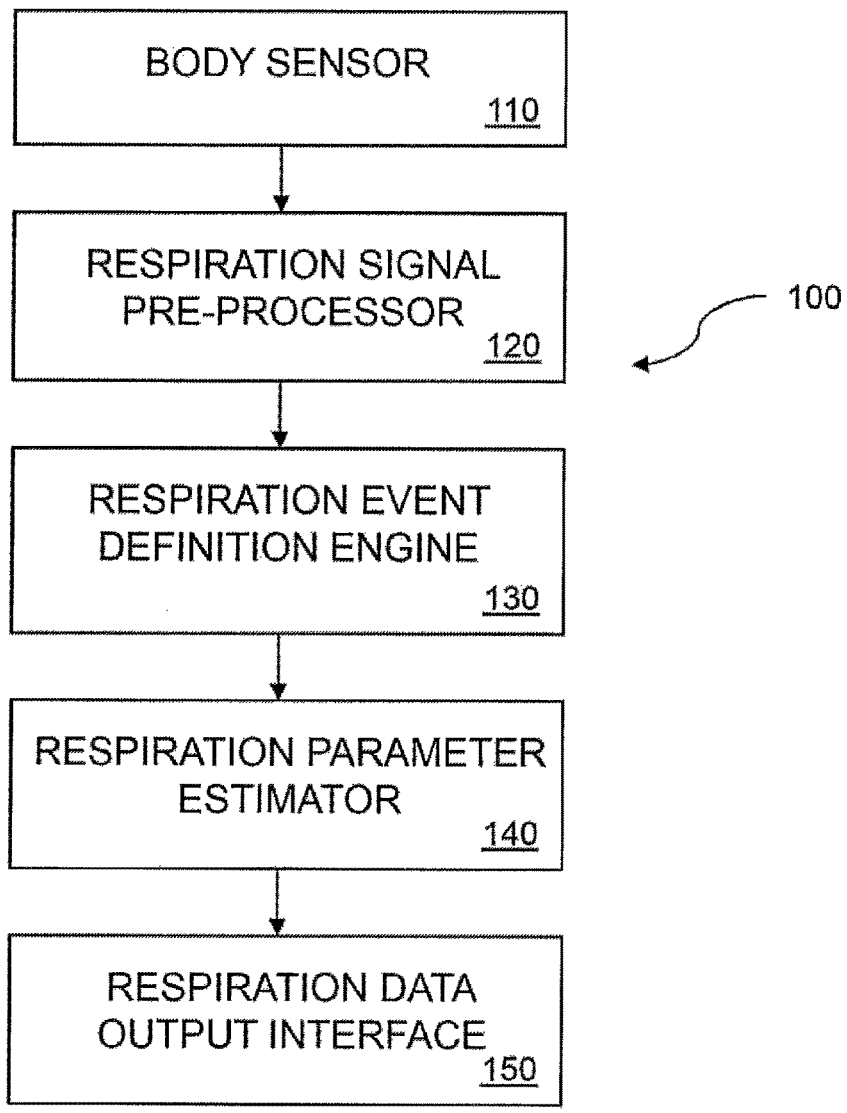
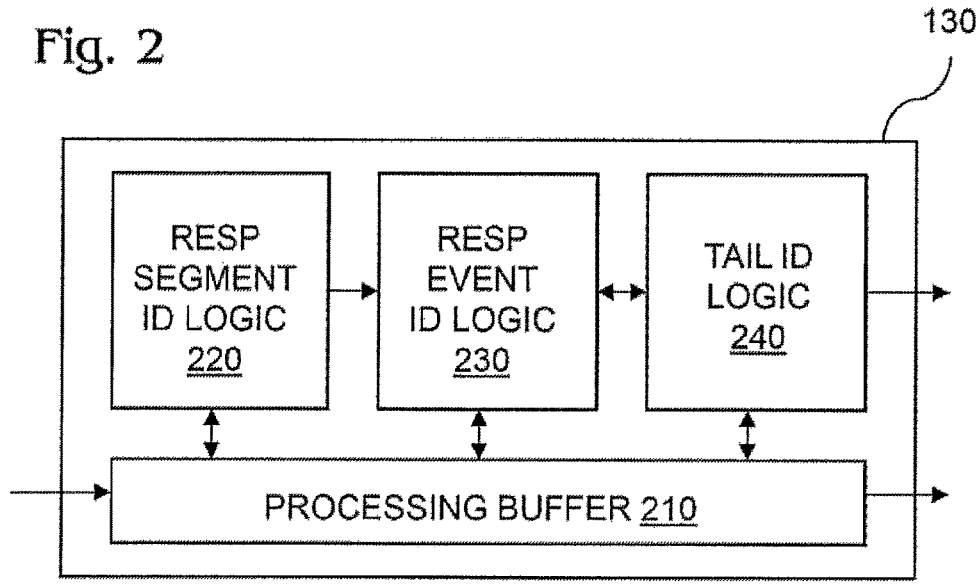

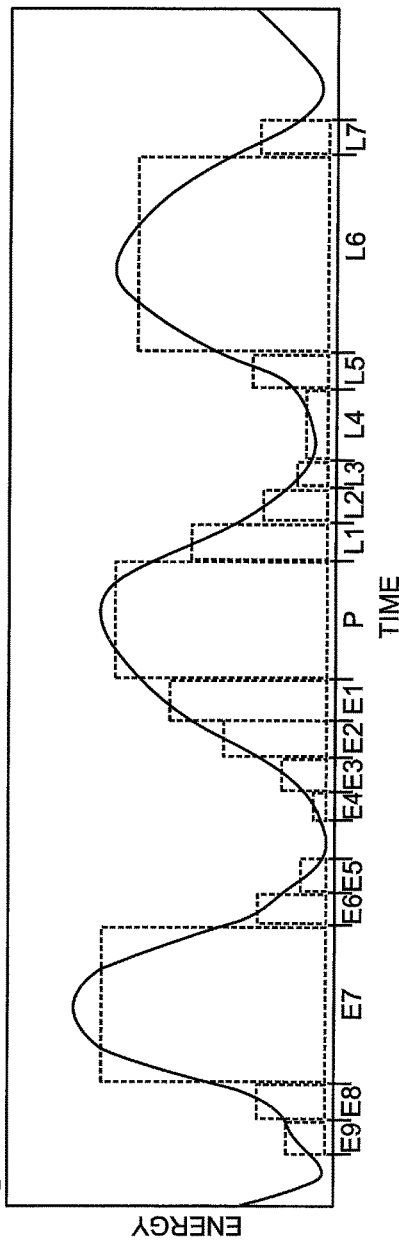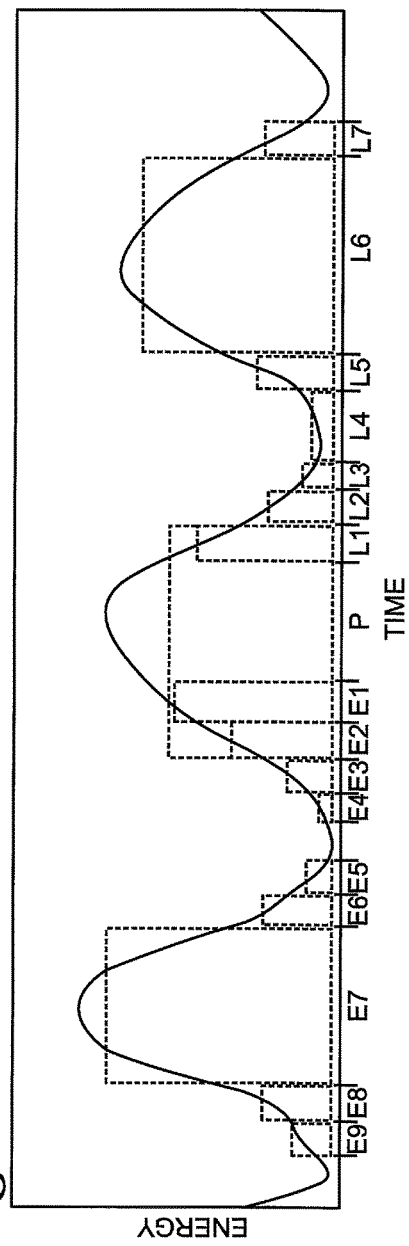

METHOD AND ENGINE FOR DEFINING RESPIRATION EVENTS IN BODY SENSOR SIGNALS

BACKGROUND OF THE INVENTION

The present invention relates to respiration monitoring and, more particularly, defining respiration events in body sensor signals.

Respiration is an important vital sign in health monitoring applications. Abnormal respiration, as reflected by a high or low respiration rate or inspiration to expiration ratio (I:E) or other respiration parameter, can indicate a current or imminent acute health problem, such as an asthma attack or cardiac arrest.

Many different kinds of respiration monitoring devices are known. One class of devices monitors end-tidal carbon dioxide ($EtCO_2$) expelled by a patient. Another monitors air pressure through the patient's airways. Another monitors breath sounds emanating from the patient's body. Still others monitor chest movement associated with a patient's breathing using a belt, Doppler detector or video camera. A common feature of these monitoring devices is that they generate a body sensor signal that can be processed to identify respiration events (i.e. inspiration and expiration events) from which respiration parameters, such as respiration rate and I:E, can be estimated.

Unfortunately, the processing algorithms employed by these monitoring devices to identify respiration events have left something to be desired. Some of these algorithms have been prone to error. For example, some algorithms often misinterpret narrow gaps in respiration energy as a respiration event boundaries or misinterpret sustained low-level respiration energy before or after respiration events as a continuation of these events. Moreover, some algorithms suffer from a lack of cross-compatibility. For example, algorithms used by $EtCO_2$ monitoring devices are generally not compatible with acoustic monitoring devices, and vice versa.

SUMMARY OF THE INVENTION

The present invention provides a method and engine for defining respiration events in body sensor signals that are highly accurate and compatible with many different classes of respiration monitoring devices. The present method and engine provide improved respiration event definition through the expedients of dynamic thresholding, segment merging and tail identification.

In one aspect of the invention, a method for defining respiration events in a body sensor signal comprises receiving the signal; identifying respiration segments in the signal; selectively merging adjacent ones of the segments into a respiration event through application of segment merger rules; selectively identifying ones of the segments in the event as tail segments through application of tail identification rules; and outputting information regarding the event.

In some embodiments, each of the segments is identified by identifying a peak sample in the signal as a starting sample of the segment and expanding the segment about the peak sample to include bordering samples in a sample-wise operation wherein a height of a bordering sample being evaluated for inclusion in the segment is compared with a dynamic threshold updated as a function of heights of one or more samples already included in the segment.

In some embodiments, adjacent ones of the segments are selected for merger into the event by identifying a parent segment as a starting sample of the event and expanding the event about the parent segment to selectively include adjacent ones of the segments in a segment-wise operation through application of the merger rules.

In some embodiments, one or more of the merger rules uses a height of a parent segment of the event as an input.

In some embodiments, one or more of the merger rules uses a height of a segment being evaluated for inclusion in the event as an input.

In some embodiments, one or more of the merger rules uses a height of a gap between the event and a segment being evaluated for inclusion in the event as an input.

In some embodiments, one or more of the merger rules uses a width of a parent segment of the event as an input.

In some embodiments, one or more of the merger rules uses a width of a segment being evaluated for inclusion in the event as an input.

In some embodiments, one or more of the merger rules uses a width of a gap between the event and a segment being evaluated for inclusion in the event as an input.

In some embodiments, one or more of the merger rules uses an indication of whether a segment already included in the event has been identified as a tail segment as an input.

In some embodiments, one or more of the tail identification rules uses a height of a segment being evaluated for identification as a tail segment as an input.

In some embodiments, one or more of the tail identification rules uses a height of a segment already identified as a tail segment as an input.

In some embodiments, the signal comprises an energy envelope.

In some embodiments, the outputted information identifies a start and an end of the event.

In some embodiments, the outputted information identifies a start and an end of a tail of the event.

In some embodiments, the event is one of an inspiration or expiration event.

In another aspect of the invention, a method for defining respiration events in a body sensor signal comprises receiving the signal; identifying respiration segments in the signal; selectively merging adjacent ones of the segments into a respiration event by identifying a parent segment as a starting segment of the event and expanding the event about the parent segment to selectively include adjacent ones of the segments in a segment-wise operation based on application of segment merger rules; and outputting information regarding the event.

In another aspect of the invention, a respiration event definition engine comprises a processing buffer configured to receive a body sensor signal; respiration segment identification logic configured to identify respiration segments in the signal; respiration event identification logic configured to merge selected adjacent ones of the segments into a respiration event through application of segment merger rules; and tail identification logic configured to identify selected ones of the segments in the event as tail segments through application of tail identification rule, wherein the engine is configured to output information regarding the event.

These and other aspects of the invention will be better understood by reference to the following detailed description taken in conjunction with the drawings that are briefly described below. Of course, the invention is defined by the appended claims.

BRIEF DESCRIPTION OF THE DRAWINGS

FIG. 1 shows a respiration monitoring device.

FIG. 2 shows a respiration event definition engine.

FIG. 14 shows an exemplary respiration event in a body sensor signal before selectively merging respiration segments into the event or selectively identifying segments in the event as tail segments.

FIG. 15 shows an exemplary respiration event in a body sensor signal after selectively merging respiration segments into the event and selectively identifying segments in the event as tail segments.

DETAILED DESCRIPTION OF A PREFERRED EMBODIMENT

Figure 3:
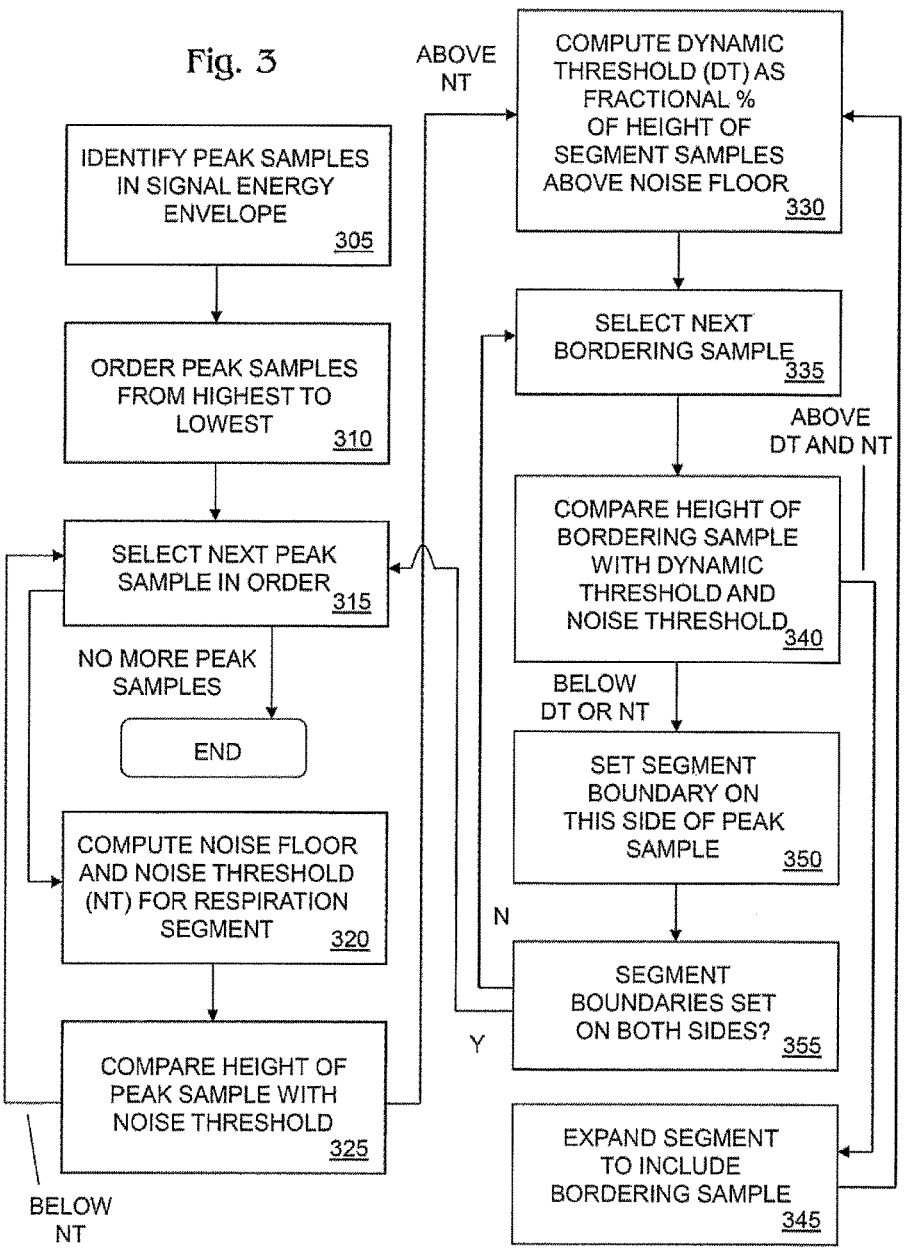
FIG. 3 shows a method for identifying respiration segments in a body sensor signal.

FIG. 1 shows a respiration monitoring device 100 in some embodiments of the invention. Device 100 has a body sensor 110 that generates a body sensor signal having samples that capture breathing (i.e. inspiration and expiration) of a human patient being monitored. Body sensor 110 may take various forms. Body sensor 110 may be an acoustic sensor that has a microphone capturing breath sounds. Alternatively, body sensor 110 may capture end-tidal carbon dioxide ($EtCO_2$) expelled by a patient; or air pressure through a patient's airways; or chest movement associated with a patient's breathing using a belt, Doppler detector or video camera. Body sensor 110 continually transmits a body sensor signal waveform to respiration signal preprocessor 120.

Respiration signal preprocessor 120 preprocesses the body sensor signal waveform received from body sensor 110 to prepare the signal for processing by event definition engine 130. Preprocessor 120 filters, rectifies and generates an energy envelope of the signal waveform. Preprocessor 120 may perform other preparatory operations on the signal waveform, such as noise spike removal. Preprocessor 120 continually transmits the energy envelope to respiration event definition engine 130.

In FIG. 2, event definition engine 130 is shown to include a processing buffer 210, respiration segment identification logic (RESP SEGMENT ID LOGIC) 220, respiration event identification logic (RESP EVENT ID LOGIC) 230 and tail identification logic (TAIL ID LOGIC) 240. Processing buffer 210 is a storage element that receives the body sensor signal energy envelope from preprocessor 120. At a given time, buffer 210 holds samples representing a predetermined number of seconds of the energy envelope (e.g. 30 seconds).

Buffer 210 may be a rolling buffer wherein every predetermined number of seconds (e.g. every one second) the oldest portion of the energy envelope held in buffer 210 is replaced with a new portion. Logic elements 220, 230, 240 operate on the energy envelope currently held in processing buffer 210. In the description of these operations that follows, "height" is a measure of energy and "width" is a measure of duration. The height of a respiration segment is the mean energy of all samples in the segment relative to a noise floor. The height of a gap between respiration segments is the mean energy of all samples in the gap relative to the noise floor. A minimum gap height is set at one-half times the noise floor. The noise floor is computed relative to a respiration segment designated as a parent segment.

Respiration segment identification logic 220 identifies respiration segments in the energy envelope currently held in processing buffer 210. FIG. 3 illustrates a respiration segment identification method performed by logic 220 in some embodiments of the invention.

In the exemplary method, logic 220 first identifies peak samples in the energy envelope (305). Peak samples are samples having adjacent samples on each side of lower height.

Next, logic 220 orders the peak samples from highest to lowest (310).

Next, logic 220 selects the next peak sample in the order (315). The peak sample is the starting sample of a respiration segment. The segment expands sample-wise about the peak sample to include additional samples as described herein. The first peak sample selected is the highest peak sample in the energy envelope and the last peak sample selected is the lowest peak sample in the energy envelope. The flow terminates when all peak samples in the order have been selected and processed.

Next, logic 220 computes a noise floor and a noise threshold (NT) for the respiration segment using the peak sample (320). To compute the noise floor, logic 220 orders a group of contiguous samples on one side of the peak sample over a predetermined time period, such as five seconds, from highest to lowest. Logic 220 then computes the above-ground height of a predetermined fractional percentage of the group, such as ten percent, which have the lowest height. Logic 220 then repeats these operations for a group of contiguous samples on the other side of the peak sample and computes the noise floor for the segment as the mean of the above-ground heights computed from the respective sides. The noise threshold may be computed as a function of the noise floor for the segment, such as two times the noise floor, or may be a constant value.

Next, logic 220 compares the height of the peak sample with the noise threshold for the respiration segment (325). If the height of the peak sample is below the noise threshold, no respiration segment will be created from the peak sample and the flow returns to Step 315 where the next peak sample (if any) is selected. On the other hand, if the height of the peak sample is above the noise threshold, a respiration segment will be created from the peak sample and the flow proceeds.

Next, logic 220 computes a dynamic threshold (DT) as a fractional percentage, such as 33.3 percent, of the height above the noise floor of the samples in the respiration segment (330). Initially, the peak sample is the only sample in the segment and therefore the only sample used in computing the dynamic threshold. However, the number of samples used in computing the dynamic threshold increases as the segment expands sample-wise about the peak sample to include additional samples.

Next, logic 220 selects a bordering sample (335). The bordering sample is the closest sample outside the respiration segment on one side or the other. Since the peak sample is the starting sample in the segment, the first bordering sample is the sample just before or after the peak sample. As the segment expands sample-wise about the peak sample to include bordering samples, the closest outside sample on one side or other of the expanded segment becomes the new bordering sample. To avoid bias, logic 220 may alternate between the two sides of the peak sample (e.g., left-right-left) when selecting bordering samples until a boundary is established on one side of the peak sample as described herein, whereupon logic 220 selects all further bordering samples from the other side of the peak sample.

Next, logic 220 compares the height of the bordering sample with the dynamic threshold and the noise threshold (340). If the height of the bordering sample is above the dynamic threshold and the noise threshold, logic 220 expands the respiration segment to include the bordering sample (345) and re-computes the dynamic threshold to take into account the bordering sample (330). On the other hand, if the height of the bordering sample is below the dynamic threshold or the noise threshold, logic 220 establishes a boundary for the segment on the side of the peak sample where the bordering sample resides just inside the bordering sample (350) and determines whether boundaries have been established for both sides of the segment (355). If boundaries have not been established for both sides of the segment, the segment is not fully bounded and the flow returns to Step 330. If boundaries have been established for both sides of the segment, the segment is fully bounded and the flow returns to Step 315 where the next peak sample (if any) is selected and identification of the next respiration segment begins.

Figure 5:
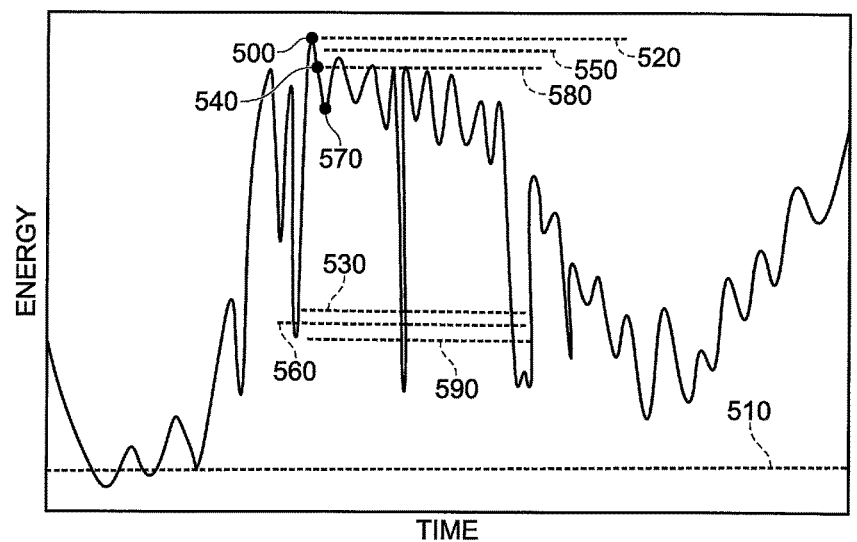
FIG. 5 shows an example of respiration segment identification in a signal.

FIG. 5 shows an example of respiration segment identification in a body sensor signal energy envelope held in processing buffer 120. A peak sample 500 is selected and a noise floor 510 and noise threshold are computed using peak sample 500. Since peak sample 500 is above the noise threshold, a segment will be computed using peak sample 500 as a starting point and an initial segment height 520 above noise floor 510 is computed from the samples that are part of the segment. Since peak sample 500 is, at first, the only sample in the segment, initial segment height 520 is the height of peak sample 500. An initial dynamic threshold 530 is then computed as a fractional percentage of initial height 520. A bordering sample 540 is then selected and the height of bordering sample 540 is compared with the dynamic threshold and the noise threshold. Since the height of bordering sample 540 is above both the dynamic threshold and the noise threshold, the segment is expanded to include bordering sample 540 and the dynamic threshold is recomputed to take into account the expansion. That is to say, a new segment height 550 above noise floor 520 is computed as the mean energy of the group of samples 500, 540 that are part of the expanded segment and a new dynamic threshold 560 is computed as a fractional percentage of new segment height 550. The next bordering sample 570 is then selected and the height of bordering sample 570 is compared with new dynamic threshold 560 and the noise threshold, resulting in further expansion of segment to include bordering sample 570 and further updating of segment height 580 and dynamic threshold 590. The process continues until the heights of bordering samples on both sides of peak sample 500 are found to be below either the dynamic threshold or the noise threshold, at which point the segment is fully bounded and identification of the next respiration segment begins.

Figure 6:
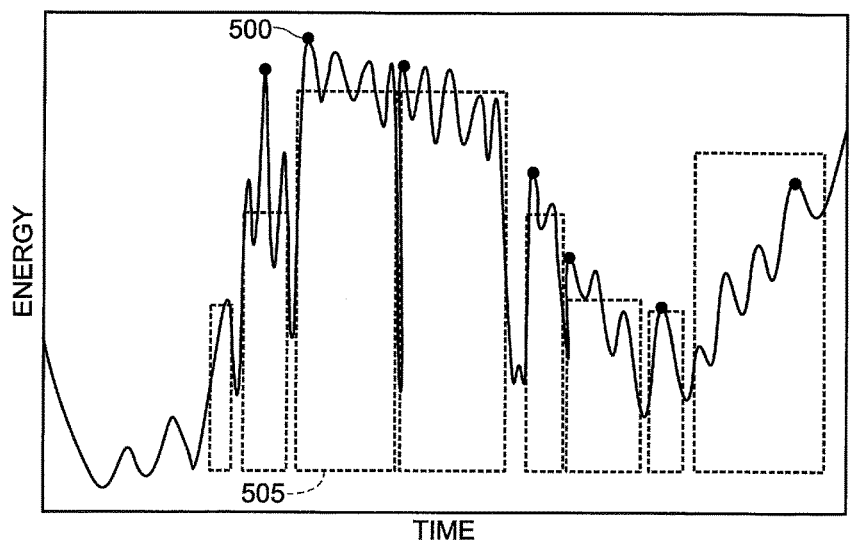
FIG. 6 shows an example of respiration segments identified in the signal.

FIG. 6 shows respiration segments identified in the body sensor signal energy envelope after respiration segment identification has been completed. The segments include segment 505 consisting of a group of contiguous samples identified using peak sample 500 as a starting point as well as other segments each consisting of groups of contiguous samples identified using other peak samples as starting points. The segments are separated by gaps each consisting of groups of contiguous samples. However, in some instances, adjacent segments may not have a gap between them, but may be identified as discrete segments by virtue of having very different heights.

Logic 220 conveys the results of respiration segment identification in the body sensor signal energy envelope to respiration event identification logic 230.

Figure 4:
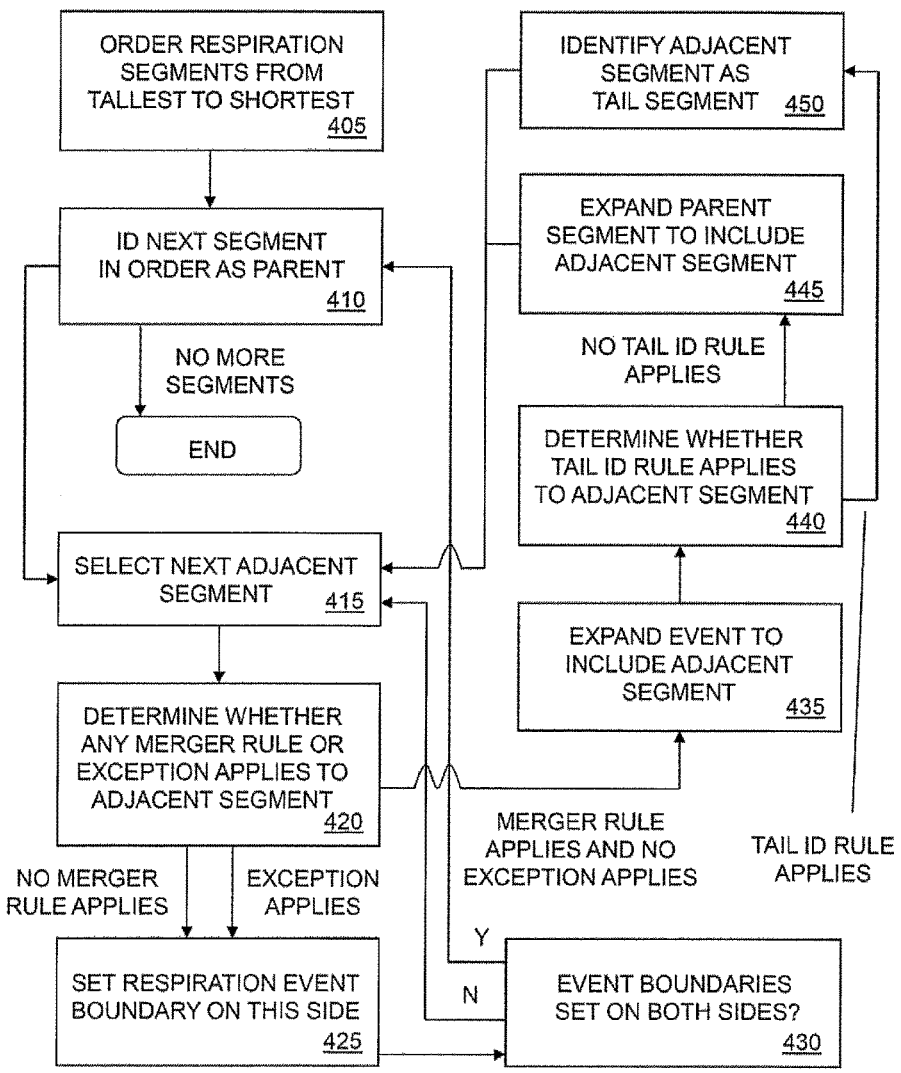
FIG. 4 shows a method for selectively merging adjacent respiration segments in a body sensor signal into a respiration event and selectively identifying segments in the event as tail segments.

Respiration event identification logic 230 identifies respiration events by selectively merging adjacent respiration segments. Respiration events include inspiration events and expiration events. Logic 230 then conveys the results of respiration event identification to tail identification logic 240, which selectively identifies segments included in the events as tail segments. FIG. 4 shows a segment merger and tail identification method performed by logic elements 230, 240 in some embodiments of the invention.

In the exemplary method, logic 230 first orders the respiration segments identified by logic 220 from tallest to shortest (405). As mentioned, the height of a respiration segment is the mean energy of all samples in the segment above the noise floor for the segment. Thus, the tallest segment is the segment having the highest mean energy above its noise floor and the shortest segment is the segment having the lowest mean energy above its noise floor.

Next, logic 230 identifies the next respiration segment in the order as the parent segment of a respiration event (410). The parent segment is the starting segment of a respiration event. The event expands segment-wise about the parent segment to include additional segments as described herein. The tallest segment is identified as the first parent segment, the next tallest segment is identified as the second parent segment, and so on. However, segments that have been merged into an event associated with an earlier identified parent segment are removed from the order. The flow terminates when all segments have either been identified as a parent segment and processed or merged into an event associated with an earlier identified parent segment.

Next, logic 230 selects a respiration segment adjacent to the respiration event associated with the parent segment (415). The adjacent segment is the closest segment outside the event on one side or the other. Since the parent segment is the starting segment of the event, the first adjacent segment is the segment just before or after the parent segment. As the event expands segment-wise about the parent segment to include additional segments, the closest outside segment on one side or other of the expanded event becomes the new adjacent segment. An adjacent segment may be added to an event as part of the parent segment or as a tail segment as described herein. To avoid bias, logic 230 may alternate between the two sides of the event (e.g., left-right-left) when selecting adjacent segments until a boundary is established on one side of the event as described herein, after which logic 230 always selects the adjacent segment from the other side of the event.

Next, logic 230 determines whether any segment merger rule or merger exception applies to the adjacent segment (420). Segment merger rules are guidelines for determining whether the adjacent segment should be considered part of the respiration event associated with the parent segment (e.g. part of the same instance of inspiration or expiration), either by expanding the parent segment to include the adjacent segment or by adding the adjacent segment to the event as a tail segment. Merger rules are based on empirically observed human breathing patterns and use various body sensor signal components as inputs, including the height of the parent segment, the height of the adjacent segment, the height of the gap between the event and the adjacent segment, the width of the parent segment, the width of the adjacent segment, the width of the gap between the event and the adjacent segment, the noise floor of the parent segment, and whether or not any segment already included in the event has been identified as a tail segment.

If logic 230 determines that none of the segment merger rules applies, or that a merger exception applies, logic 230 establishes a boundary for the respiration event on the side where the adjacent segment resides (without adding the adjacent segment to the event) (425) and determines whether boundaries have been established for both sides of the event (430). If boundaries have not been established for both sides of the event, the event is not fully bounded and the flow returns to Step 415. If boundaries have been established for both sides of the event, the event is fully bounded and the flow returns to Step 410 where the next segment in tallest-to-shortest order (if any remains) is identified as the new parent segment and is processed.

On the other hand, if logic 230 determines that a segment merger rule applies and that no merger exception applies, logic 230 expands the respiration event to include the adjacent segment (435) and invokes tail identification logic 240 to determine whether the adjacent segment is a tail segment. In this regard, it has been empirically observed in the breathing patterns of some humans that respiration energy may stay at a low level over a sustained period as breathing begins or is completed without falling below a noise threshold used to detect the start or end of respiration events. Such breathing can cause respiration event boundaries to be misinterpreted. Logic 240 identifies tails of a respiration event that can be used as a substitute or supplement to noise thresholds to delimit and distinguish between respiration events.

Logic 240 first determines whether any tail identification rule applies to the adjacent segment (440). Tail identification rules are guidelines for determining whether an adjacent segment added to a respiration event should be deemed part of the parent segment or identified as a tail segment. Tail identification rules use various body sensor signal components as inputs, including the width of the parent segment, the height of the parent segment, the height of the adjacent segment, whether not any adjacent segment previously added to the event has been identified as a tail segment and the height of a tail segment previously added to the event.

If logic 240 determines that no tail identification rule applies, logic 240 expands the parent segment to include the adjacent segment (445). On the other hand, if logic 240 determines that a tail identification rule applies, logic 240 identifies the adjacent segment as a tail segment (450). In either event, the flow returns to Step 415, where consideration is given to whether to merge the next adjacent segment (if any) into the expanded respiration event.

Logic 240 conveys the results of respiration event and tail identification in the body sensor signal energy envelope to respiration parameter estimator 140.

Respiration parameter estimator 140 applies the results of respiration event and tail identification in the body sensor signal envelope to compute respiration parameters, such as respiration rate and I:E, and transmits to respiration data output interface 150 output data generated based at least in part on these respiration parameters. Data output interface 150 may, for example, display the output data locally, relay them to a remote clinician facility, or both.

The following segment merger rules, segment merger exception and tail identification rules are operative in some embodiments of the invention:

Segment Merger Rules

Figure 7:
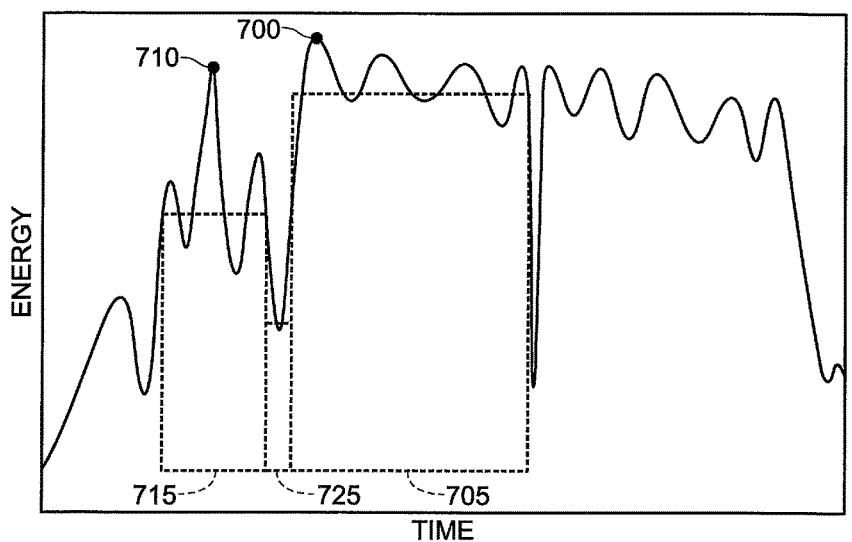
FIG. 7 shows exemplary signal elements used in a first merger rule.

Merger Rule 1. The adjacent segment is merged into the respiration event if: (a) the ratio of the height of the adjacent segment to the height of the gap between the event and the adjacent segment is less than a predetermined ratio (e.g. 2); and (b) the width of the gap is narrower than a predetermined width (e.g. 40 milliseconds). This rule reflects the empirical observation that an adjacent segment is likely part of a respiration event if the gap between the event and the adjacent segment is sufficiently shallow and narrow. FIG. 7 illustrates this rule. Parent segment 705 is identified using peak sample 700 as a starting point and adjacent segment 715 is identified using peak sample 710 as a starting point. Parent segment 705 and adjacent segment 715 are separated by a gap 725. Since the height of adjacent segment 615 is less than twice the height of gap 725 and the width of gap 725 is less than 40 ms, the rule applies and adjacent segment 715 is merged into the respiration event associated with parent segment 705.

Figure 8:
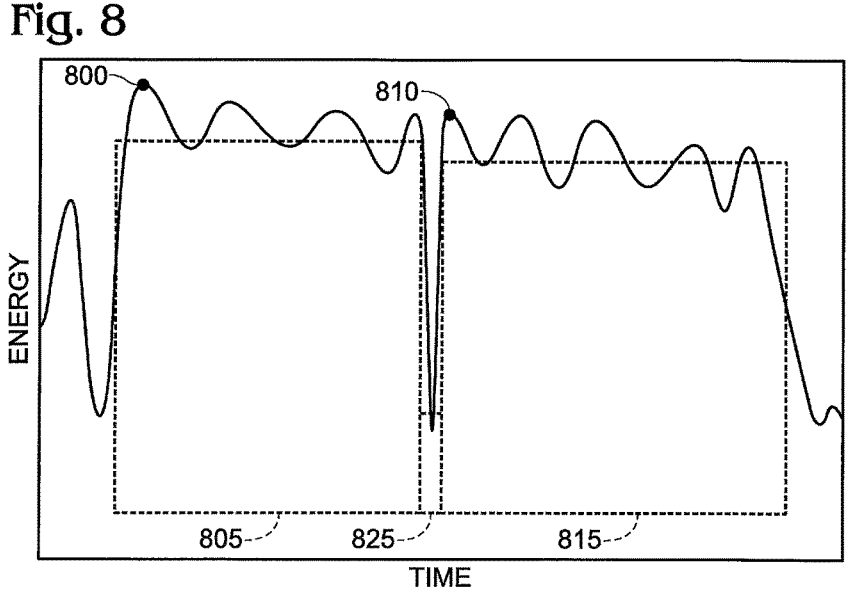
FIG. 8 shows exemplary signal elements used in a second merger rule.

Merger Rule 2. The adjacent segment is merged into the respiration event if: (a) the ratio of the height of the adjacent segment to the height of the gap between the event and the adjacent segment is less than a predetermined ratio (e.g. 8); (b) the width of the gap is narrower than a predetermined width (e.g. 40 ms); and (c) the ratio of the width of the wider of the adjacent segment and the parent segment to the width of the gap, multiplied by the ratio of the height of the gap to the height of the adjacent segment, is greater than a predetermined ratio (e.g. 10). This rule reflects the empirical observation that for an adjacent segment to be part of a respiration event, as the gap between the event and the adjacent segment deepens or widens, the wider of the parent segment and the adjacent segment must widen or the height of the adjacent segment must decrease. FIG. 8 illustrates this rule. Parent segment 805 is identified using peak sample 800 as a starting point and adjacent segment 815 is identified using peak sample 810 as a starting point. Parent segment 805 and adjacent segment 815 are separated by a gap 825. Since the height of adjacent segment 815 is less than eight times the height of gap 825, the width of gap 820 is narrower than 40 ms, and the ratio of the width of adjacent segment 815 to the width of gap 825, multiplied by the ratio of the height of gap 825 to the height of adjacent segment 815, is greater than ten, the rule applies and adjacent segment 815 is merged into the respiration event associated with parent segment 805.

Figure 9:
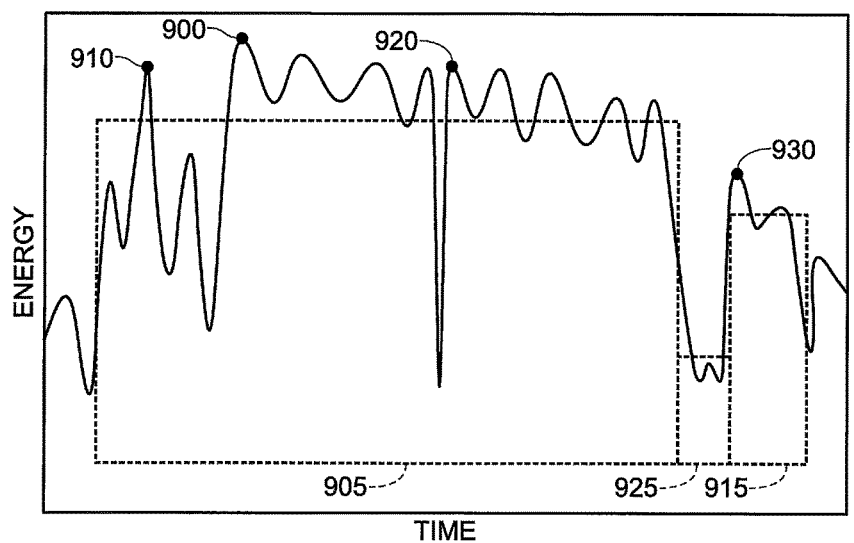
FIG. 9 shows exemplary signal elements used in a third merger rule.

Merger Rule 3. The adjacent segment is merged into the respiration event if: (a) the ratio of the height of the adjacent segment to the height of the gap between the event and the adjacent segment is less than a predetermined ratio (e.g. 8); (b) the width of the gap is narrower than a predetermined width (e.g. 40 ms); and (c) the ratio of the width of the parent segment to the width of the adjacent segment, multiplied by the ratio of the height of the parent segment to the height of the adjacent segment, multiplied by the ratio of the height of the gap to the height of the adjacent segment, multiplied by the ratio of a predetermined width (e.g. 40 ms) to the width of the gap, is greater than a predetermined ratio (e.g. 2). This rule reflects the empirical observation that a sufficiently narrow adjacent segment following a sufficiently wide parent segment of a respiration event is likely part of the event since gaps are commonplace at the end of long events. FIG. 9 illustrates this rule. Parent segment 905 is the product of the merger of three segments identified using peak samples 900, 910, 920 as starting points. Adjacent segment 915 is identified using peak sample 930 as a starting point. Parent segment 905 and adjacent segment 915 are separated by a gap 925. Since the height of adjacent segment 915 is less than eight times the height of gap 925, the width of gap 925 is less than 40 ms, and the ratio of the width of parent segment 905 to the width of adjacent segment 915, multiplied by the ratio of the height of parent segment 905 to the height of adjacent segment 915, multiplied by the ratio of the height of gap 925 to the height of adjacent segment 915, multiplied by the ratio of 40 ms to the width of gap 925, is greater than two, the rule applies and adjacent segment 915 is merged into the respiration event associated with parent segment 905.

Figure 10:
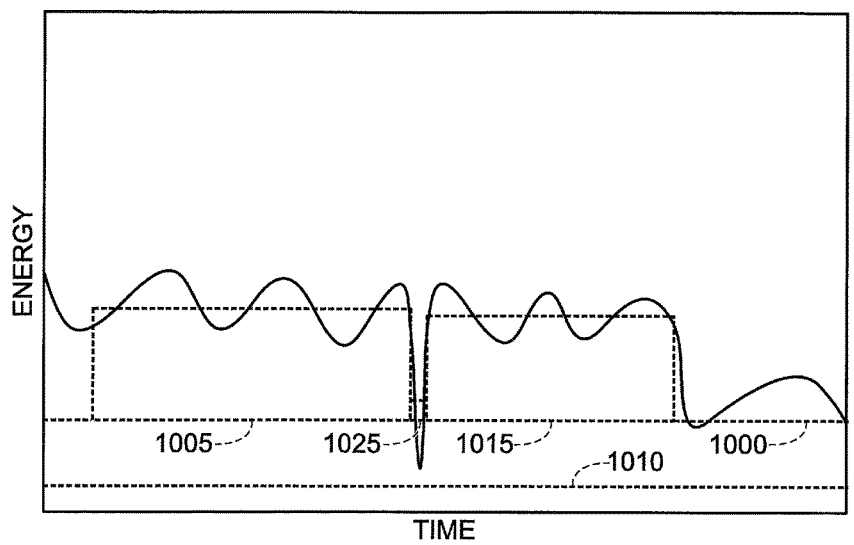
FIG. 10 shows exemplary signal elements used in a fourth merger rule.

Merger Rule 4. The adjacent segment is merged into the respiration event if: (a) the ratio of the height of the parent segment to the noise floor for the parent segment is less than a predetermined ratio (e.g. 4); and (b) the width of the gap between the parent segment and the adjacent segment is narrower than a predetermined width (e.g. 20 ms). This rule reflects the empirical observation that an adjacent segment is likely part of a respiration event if the event is a sufficiently low-energy event and the gap between the adjacent segment and the event is sufficiently narrow. FIG. 10 illustrates this rule. Parent segment 1005 and adjacent segment 1015 are separated by a gap 1025. Since the height of parent segment 1005 (above noise floor 1000) is less than four times the height of noise floor 1000 (above ground 1010) and the width of gap 1025 is narrower than 20 ms, the rule applies and adjacent segment 1015 is merged into the respiration event associated with parent segment 1005.

Figure 11:
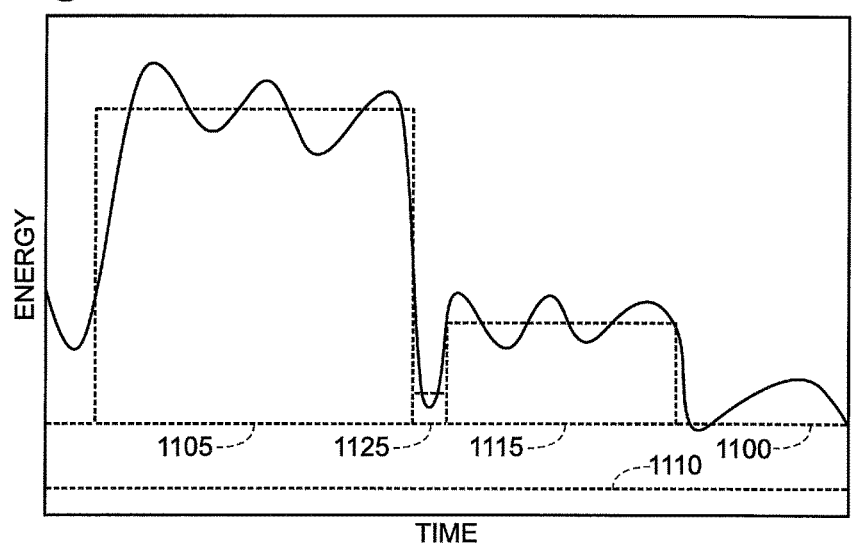
FIG. 11 shows exemplary signal elements used in a fifth merger rule.

Merger Rule 5. The adjacent segment is merged into the respiration event if: (a) the ratio of the height of the parent segment to the height of the gap between the parent segment and the adjacent segment is less than a predetermined ratio (e.g. 8); (b) the width of the gap is narrower than a predetermined width (e.g. 40 ms); and (c) the ratio of the width of the wider of the parent segment and the adjacent segment to the width of the gap, multiplied by the ratio of the height of the gap to the height of the adjacent segment, multiplied by the ratio of the height of the noise floor for the adjacent segment to the height of the adjacent segment, is greater than a predetermined ratio (e.g. 1). This rule reflects the empirical observation that a sufficiently low-energy adjacent segment following a sufficiently wide respiration event is likely part of the event since gaps are commonplace at the end of long events. FIG. 11 illustrates this rule. Parent segment 1105 and adjacent segment 1115 are separated by a gap 1125. Since the height of parent segment 1105 is less than eight times the height of gap 1125, the width of gap 1125 is narrower than 40 ms, and the ratio of the width of parent segment 1105 to the width of gap 1125, multiplied by the ratio of the height of gap 1125 to the height of adjacent segment 1115, multiplied by the ratio of the height of noise floor 1100 (above ground 1110) to the height of adjacent segment 1115 (above noise floor 1100) is greater than a one, the rule applies and adjacent segment 1115 is merged into the respiration event associated with parent segment 1105.

Figure 12:
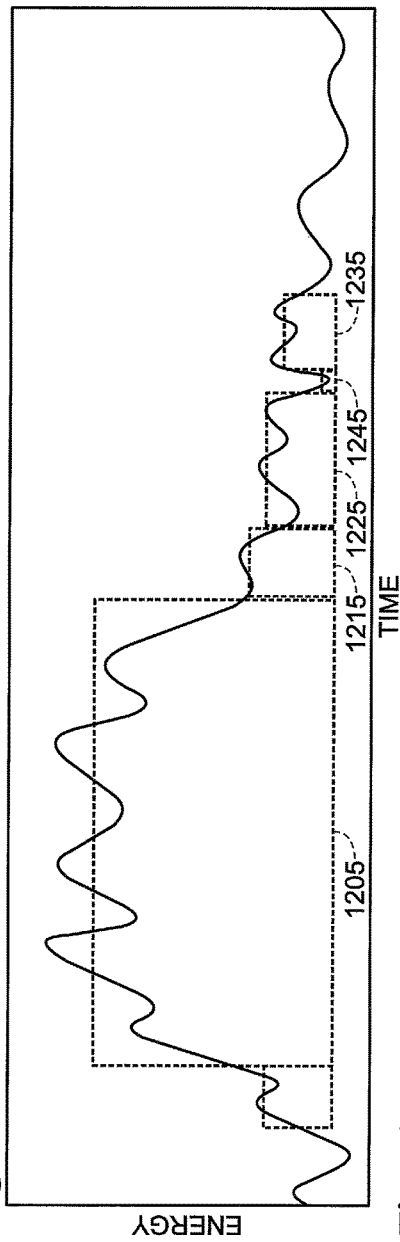
FIG. 12 shows exemplary signal elements used in a sixth merger rule.

Merger Rule 6. The adjacent segment is merged into the respiration event if: (a) the ratio of the height of the adjacent segment to the height of the gap between the parent segment and the adjacent segment is less than a predetermined ratio (e.g. 8); (b) the width of the gap is narrower than a predetermined width (e.g. 80 ms); and (c) the ratio of the sum of the width of the parent segment and the widths of already classified tail segments on the same side as the adjacent segment to the width of the gap, multiplied by the ratio of the height of the parent segment to the height of the adjacent segment, multiplied by the ratio of the height of the gap to the height of the adjacent segment, multiplied by the ratio of a predetermined width (e.g. 40 ms) to the width of the gap, is greater than a predetermined ratio (e.g. 6). This rule reflects the empirical observation that an adjacent segment following a tail segment of a respiration event is likely part of the event where a larger gap exists between the adjacent segment and the tail segment than would be permitted in the absence of a tail segment since larger gaps are commonplace at event tails. FIG. 12 illustrates this rule. A respiration event includes a parent segment 1205 and tail segments 1215, 1225 on one side of parent segment 1205. (The event also includes a tail segment on the other side of parent segment 1205). On the side where tail segments 1215, 1225 reside, the event is separated from adjacent segment 1235 by a gap 1245. Since the height of adjacent segment 1235 is less than eight times the height of gap 1245, gap 1245 is narrower than 80 ms, and the ratio of the sum of the width of parent segment 1205 and the widths of tail segments 1215, 1225 to the width of gap 1245, multiplied by the ratio of the height of parent segment 1205 to the height of adjacent segment 1235, multiplied by the ratio of the height of gap 1245 to the height of adjacent segment 1235, multiplied by the ratio of 40 ms to the width of gap 1245, is greater than six, the rule applies and adjacent segment 1235 is merged into the respiration event associated with parent segment 1205.

Figure 13:
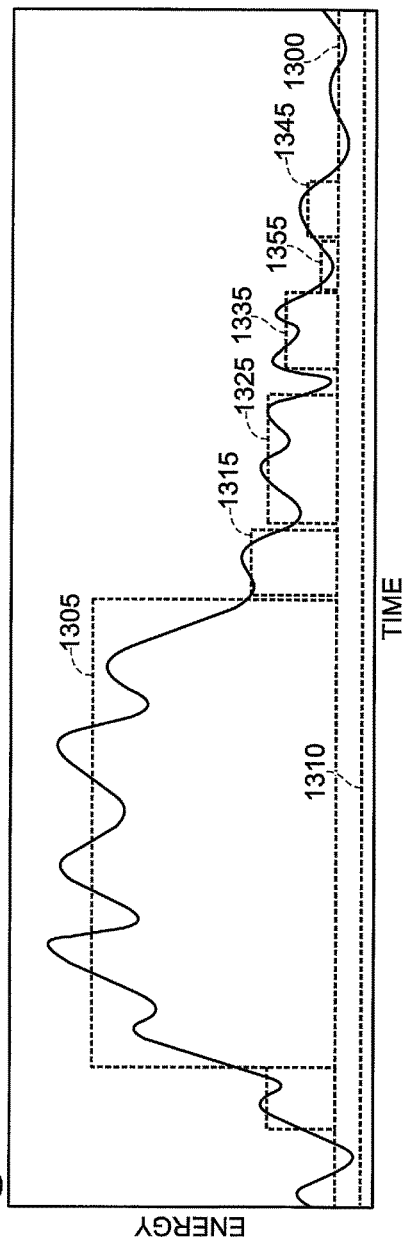
FIG. 13 shows exemplary signal elements used in a seventh merger rule.

Merger Rule 7. The adjacent segment is merged into the respiration event if: (a) the ratio of the height of the adjacent segment to the height of the gap is less than a predetermined ratio (e.g. 8); (b) the width of the gap is narrower than a predetermined width (e.g. 160 ms); (c) the ratio of the height of the adjacent segment to the noise floor of the adjacent segment is less than a predetermined ratio (e.g. 4); and (d) the ratio of the sum of the of the width of the parent segment and the widths of already classified tail segments on the same side as the adjacent segment to the width of the gap, multiplied by the ratio of the height of the parent segment to the height of the adjacent segment, multiplied by the ratio of the height of the gap to the height of the adjacent segment, multiplied by the ratio of a predetermined width (e.g. 40 ms) to the width of the gap, is greater than a predetermined ratio (e.g. 2). This rule reflects the empirical observation that an adjacent segment near its noise floor following a tail segment of a respiration event is particularly likely to be part of the event where a larger gap exists between the adjacent segment and the tail segment than would normally be permitted. FIG. 13 illustrates this rule. A respiration event includes a parent segment 1305 and tail segments 1315, 1325, 1335 on one side of parent segment 1305. (The event also includes a tail segment on the other side of parent segment 1305). On the side where tail segments 1315, 1325, 1335 reside, the event is separated from adjacent segment 1345 by a gap 1355. Since the height of adjacent segment 1345 is less than eight times the height of gap 1355, gap 1355 is narrower than 160 ms, the height of adjacent segment 1345 (above noise floor 1300) is less than four times the height of noise floor 1300 (above ground 1310), and the ratio of the sum of the width of parent segment 1305 and the widths of tail segments 1315, 1325, 1335 to the width of gap 1355, multiplied by the ratio of the height of parent segment 1305 to the height of adjacent segment 1345, multiplied by the ratio of the height of gap 1355 to the height of adjacent segment 1345, multiplied by the ratio of 40 ms to the width of gap 1355 is greater than two, the rule applies and adjacent segment 1345 is merged into the respiration event associated with parent segment 1305.

Segment Merger Exceptions

Merger Exception 1: If the adjacent segment is already part of another respiration event (parent segment or tail segment), the adjacent segment is not merged into the current respiration event even if one or more segment merger rules would otherwise apply.

Merger Exception 2: If the respiration event already includes one or more tail segments on the same side as the adjacent segment and the height of the adjacent segment is more than a predetermined fractional percentage (e.g. 20 percent) above the height of the adjacent tail segment, the adjacent segment is not merged into the respiration event even if one or more segment merger rules would otherwise apply.

Tail Identification Rules

Tail Identification Rule 1. Identify the adjacent segment selected for merger into the respiration event as a tail segment if a segment already included in the event on the same side as the adjacent segment has been identified as a tail segment.

Tail Identification Rule 2. Identify the adjacent segment selected for merger into the respiration event as a tail segment if: (a) no segment already included in the event that is on the same side as the adjacent segment has been identified as a tail segment; (b) the width of the parent segment is greater than a predetermined width (e.g. 100 ms); and (c) the ratio of the height of the parent segment to the height of the adjacent segment is greater than a predetermined ratio (e.g. 3).

FIGS. 14 and 15 show an exemplary respiration event in a body sensor signal before and after merging selected respiration segments into the event and identifying selected segments in the event as tail segments. The event initially includes parent segment P. Through application of segment merger rules, the event expands segment-wise about parent segment P. Adjacent segments E1, E2 and L1 are absorbed into parent segment P and adjacent segments E3, E4, L2, L3 and L4 are appended as tail segments.

The processing performed by respiration event definition engine 130 may be realized by executing software instructions under microprocessor control, in custom circuitry, or in some combination.

It will be appreciated by those of ordinary skill in the art that the invention can be embodied in other specific forms without departing from the spirit or essential character hereof. The present description is considered in all respects to be illustrative and not restrictive. The scope of the invention is indicated by the appended claims, and all changes that come within the meaning and range of equivalents thereof are intended to be embraced therein.

What is claimed is:

1. A method for improved identification of actual respiration events by reducing misidentified respiration events, comprising:

detecting potential respiration activity using a body sensor;

determining whether the detected potential respiration activity represents an actual respiration event by:

(a) generating a signal expressing the detected respiration activity, the signal being structured as a waveform comprising samples representing respiration energy at different times, wherein adjacent samples are combinable into respiration segments of different durations and adjacent respiration segments are combinable into respiration events of different durations, the respiration events including inspiration events and expiration events;

(b) storing the signal in a processing buffer;

(c) processing the signal stored in the processing buffer using a microprocessor executing software instructions including:

(d) identifying first respiration segments in the signal, wherein each of the first respiration segments includes a multiple of adjacent samples selected or discarded based on a peak of the segment signal being above or below a dynamic threshold;

(e) selectively merging adjacent ones of the first respiration segments into a first respiration event through application of predetermined segment merger rules; and (f) selectively identifying ones of the first respiration segments as tail segments of the first respiration event through application of predetermined tail identification rules; and based on the determining steps (a)-(f), identifying a respiration event as an actual respiration event;

converting the actual respiration event signal into respiration data; and outputting respiration data computed using the first respiration event using a data output interface.

2. The method of claim 1, wherein each of the first respiration segments is identified by identifying the peak signal sample as a starting sample of the first respiration segment and expanding the first respiration segment about the peak signal sample to include bordering samples in a sample-wise operation wherein the height of a bordering sample being evaluated for inclusion in the first respiration segment is compared with a dynamic threshold updated as a function of heights of one or more samples already included in the first respiration segment.

3. A respiration monitoring device that reduces misidentified respiration events, comprising:

a body sensor, the body sensor configured to detect respiration activity;

a processing buffer, the processing buffer configured to store a signal expressing the detected respiration activity, the signal being structured as a waveform comprising samples representing respiration energy at different times, wherein adjacent samples are combinable into respiration segments of different durations and adjacent respiration segments are combinable into respiration events of different durations, the respiration events including inspiration events and expiration events;

a microprocessor, the microprocessor configured to process the signal stored in the processing buffer by executing at least first, second, and third software instructions to ensure a respiration event is an actual respiration event, including:

the first instructions configured to identify first respiration segments in the signal, wherein each of the first respiration segments includes a multiple of adjacent samples selected based on whether the samples are greater than or less than a dynamic threshold;

the second instructions configured to merge selected adjacent ones of the first respiration segments into a first respiration event through application of predetermined segment merger rules; and the third instructions configured to identify selected ones of the first respiration segments as tail segments of the first respiration event through application of predetermined tail identification rules; and a respiration data output interface configured to output respiration data computed using the first respiration event when the first respiration event is an actual respiration event.

4. The method of claim 1, wherein:

based on the determining steps (a)-(f), identifying a respiration event as an actual respiration event in accordance with respiration parameters;

converting the actual respiration event signal into respiration data using the respiration parameters.

* * * * *